United States Patent
Exelmans

(10) Patent No.: US 7,636,423 B2
(45) Date of Patent: Dec. 22, 2009

(54) METHOD OF ASSOCIATING META-DATA OF RADIATION IMAGE WITH IMAGE

(75) Inventor: Walter Exelmans, Merksem (BE)

(73) Assignee: Agfa HealthCare N.V., Mortsel (BE)

( * ) Notice: Subject to any disclaimer, the term of this patent is extended or adjusted under 35 U.S.C. 154(b) by 206 days.

(21) Appl. No.: 11/554,782

(22) Filed: Oct. 31, 2006

(65) Prior Publication Data

US 2007/0112596 A1    May 17, 2007

Related U.S. Application Data

(60) Provisional application No. 60/737,722, filed on Nov. 17, 2005.

(30) Foreign Application Priority Data

Nov. 14, 2005    (EP)    ................... 05110713

(51) Int. Cl.
*A61B 6/00* (2006.01)
(52) U.S. Cl. ...................... 378/162; 378/165
(58) Field of Classification Search ................. 378/162, 378/165, 166
See application file for complete search history.

(56) References Cited

U.S. PATENT DOCUMENTS

| 5,282,236 | A | 1/1994 | Hayes et al. | |
| 5,745,036 | A * | 4/1998 | Clare | 340/572.1 |
| 6,271,536 | B1 | 8/2001 | Buytaert et al. | |
| 6,285,740 | B1 * | 9/2001 | Seely et al. | 378/98.9 |
| 6,533,453 | B1 | 3/2003 | Heidsieck et al. | |
| 2004/0079889 | A1 * | 4/2004 | Funabashi | 250/370.01 |
| 2005/0236593 | A1 * | 10/2005 | Ivo | 250/370.09 |
| 2006/0261296 | A1 * | 11/2006 | Heath et al. | 250/580 |

FOREIGN PATENT DOCUMENTS

| EP | 1 413 921 A1 | 4/2004 |
| EP | 1 591 950 A1 | 11/2005 |

OTHER PUBLICATIONS

European Search Report from Application No. EP 05110713, filed on Nov. 14, 2005, mailed Mar. 29, 2006.

* cited by examiner

*Primary Examiner*—Chih-Cheng G Kao
(74) *Attorney, Agent, or Firm*—Houston Eliseeva LLP

(57) ABSTRACT

Method of associating meta-data relating to a radiation image of an object with the radiation image wherein the meta-data are broadcast and are detected and associated with an activated radiation image recording device.

22 Claims, 2 Drawing Sheets

METHOD OF ASSOCIATING META-DATA OF RADIATION IMAGE WITH IMAGE

RELATED APPLICATIONS

This application claims the benefit of U.S. Provisional Application No. 60/737,722 filed Nov. 17, 2005, which is incorporated herein by this reference. In addition, this application claims priority to European Application No. 05110713.4 filed Nov. 14, 2005, which is also incorporated herein by this reference.

BACKGROUND OF THE INVENTION

In addition to classical radiography systems in which a radiographic image of a patient is recorded on film, computed radiography systems and digital radiography systems are nowadays commonly used.

Computed radiography systems are for example systems that are based on storage phosphor technology.

Digital radiography systems are systems in which a radiation image is recorded on a flat panel detector such as a CMOS, a selenium detector, or the like.

In systems in which imaging is obtained by irradiation of a patient, an animal, or an object with high energy radiation, it is important that the image and the meta-data giving information pertaining to the image are linked.

Meta-data are all kinds of data to be associated with the image such as demographic data (patient name, gender, date of birth, etc.) and data relating to the exposure such as the product of the current through the x-ray tube (mA) and the time the tube was energized (s) milliampere-second (mAs), kiloVolts (kV), exposure type, exposure view. etc.

For example in a computed radiography system in which a radiographic image of a patient is recorded on a photostimulatable phosphor screen, which is conveyed in a cassette, the meta-data are entered in a workstation or retrieved from a hospital information system or a radiology information system and transferred onto an identification device which is coupled to the cassette. Meta-data can be written into a non-volatile device for example an EEPROM device which is provided on the cassette conveying the exposed phosphor screen, or the data can be transferred through radio-frequency transmission onto a radio-frequency tag provided on the cassette or on the screen.

The identified cassette conveying an exposed photo-stimulatable phosphor screen is then fed into a read out apparatus (also referred to as a 'digitizer') where the meta-data are read from the identification device and where the radiographic image, which is stored in the phosphor screen, is read out. The radiographic image is read out by scanning the exposed photo-stimulatable phosphor screen with stimulating radiation and by converting the image-wise modulated light which is emitted by the screen upon stimulation into a digital signal representation of the radiographic image.

SUMMARY OF THE INVENTION

The above-described procedure is error prone, however, since identification and exposure are performed separate from each other so that it is possible that meta-data relating to a patient and associated exposure are written into the memory device of a cassette which carries a radiation image that does not correspond with these meta-data. Moreover, each separate step implies an extra time delay in the workflow.

The present invention relates to radiography and more particularly relates to a method for associating meta data such as identification data of a patient and/or data relating to high energy radiation exposure with data representing a radiation image.

It is also possible that the data which are written into the memory device on the cassette correspond with the intended circumstances, for example the intended or default settings of the X-ray source but which, due to various possible circumstances do not exactly represent the effectively applied exposure.

Furthermore, several prior art methods bears the risk of non-intended transfer of data to all cassettes conveying a photostimulatable phosphor screen, which are present in an exposure room.

To avoid this and to make the system selective, care should be taken that with the existing systems the cassette, which needs to be identified, is positioned within a pre-defined area. This has a limiting effect on the workflow the radiologist must follow.

It is an object of the present invention to provide a method that overcomes the above-mentioned problems associated with the prior art workflow.

In general according to one aspect, the invention features a method of associating meta-data relating to a radiation image of an object with the radiation image wherein the meta-data are broadcast and a radiation image recording device is activated when a radiation detector coupled to it detects high energy radiation whereupon a storage device coupled to the radiation image recording device is triggered to store meta-data.

In general according to one aspect, the invention features a method of associating meta-data relating to a radiation image of an object with the radiation image wherein the meta-data are broadcast and a radiation image recording device is activated when a radiation detector coupled to it detects radiation whereupon a storage device coupled to the radiation image recording device is triggered to store the meta-data, wherein the radiation detected by the radiation detector is secondary emission of radiation emitted by the object when it is irradiated.

In the context of the present invention a "radiation image recording device" refers to a recording device that is capable of recording a radiation image of an object, for example a photostimulatable phosphor screen, or a direct radiography image recording device whereas a "radiation detector" refers to a detector that is capable of detecting the presence of radiation, or not.

In one embodiment the meta-data are coupled with a radiation detector by detecting and storing these meta data.

A radiation image recording device is said to be "activated" when it is arranged to detect and store the broadcast meta-data.

A radiation detector can be provided to detect the presence of radiation whereupon the broadcast data are detected and stored by storage device associated with the radiation image recording device with which the radiation detector is coupled. Several embodiments of applicable radiation detectors are described further on.

Alternative embodiments for activating a radiation image recording device are envisaged such as activation by pressing a button, turning a knob, turning a switch, etc.

In still an alternative embodiment, a request for an identifier coupled with an radiation image recording device (e.g. of a cassette conveying such a recording device) is broadcast into the radiology room. All radiation image recording devices (or cassettes) present in the room will be able to receive the broadcast information. However, only the radiation image recording device (or cassette conveying this recording device) having a radiation detector that has detected radiation, also called an activated radiation image recording device (or cassette) will be arranged to respond to the sender of the broadcast information (e.g. workstation).

Activation can be implemented on similar ways as described with regard to the first embodiment.

Specifically, the identification device of the radiation image recording device (or cassette) that is arranged to respond and will, for example, respond by sending a unique cassette identification number and/or quadrant information (i.e. in which quadrant of the recording device recording has taken place), kVpeak, information regarding the spectrum etc.

The unique identification number can be associated with the meta data and the image data in a workstation or other database of a patient management system, such as a radiography information system (RIS).

Further advantages and embodiments of the present invention will become apparent from the following description.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
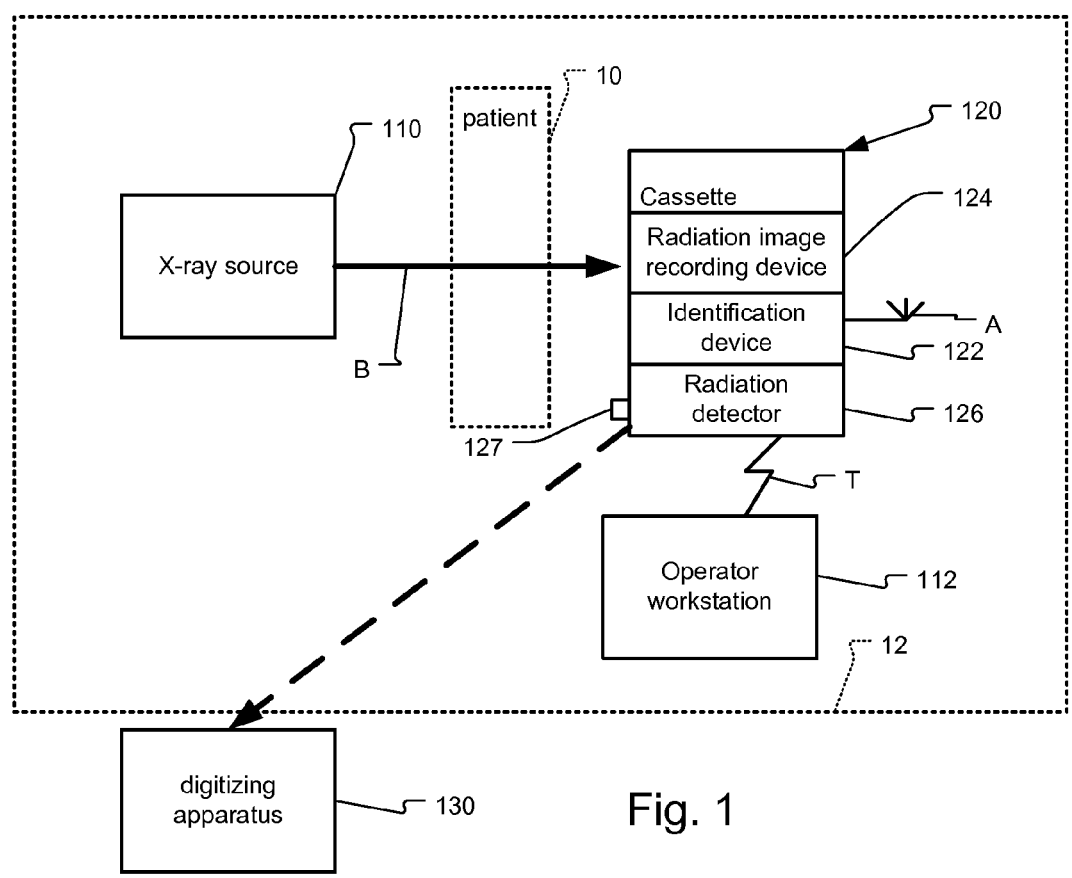
FIG. 1 is a block diagram of the inventive system.

With reference to FIG. 1, the present invention is described below with reference to a computed radiography system 100 in which a radiation image of a patient 10 is recorded on a radiation image recording device 124, e.g., photostimulable phosphor screen, which is conveyed and stored in a cassette 120. On or in the cassette 120, a radiation detector 126 is provided.

The operator first selects the metadata (also called identification data) regarding patient and/or exposure. The operator can enter the data into a workstation 112 or alternatively select them from a list which is for example provided by the radiography information system (RIS) (connected to workstation or generator console).

The meta-data usually comprise data regarding the exposure such as kV, mAs, filtering etc., as well as data regarding exposure position such as AP, PA, LL, etc. as well as identification data regarding the patient such as name, patient identification, etc. Still other types of data are possible.

Next, the exposure of an object or a patient is started with the x-ray source 110 generating the x-ray beam B, which passes through the patient 10 and in recorded on the radiation image recording device 124. This is high energy, x-ray radiation that generates an absorption contrast image, usually, by activating the phosphor material of the phosphor screen 124.

Once the exposure has been performed, the meta-data regarding exposure and/or patient are broadcast into the radiology room 12 such as from the workstation 112.

Different situations are envisaged: In one example, the cassettes which are present in the room have the ability to detect the broadcast data but only the cassette 120 to which the data pertain will store the data or, alternatively, only the cassette to which the data pertains will accept and store the data to its identification device 122.

This selectivity is obtained by means of a radiation detector 126 which generates a signal to enable acceptance and storage in identification or storage device 122 (EPROM, RFID tag, . . . ) of broadcast data once it has detected radiation (high energy or secondary radiation), as will be explained further on.

Detected and stored data are applied to a display device coupled to the cassette or the image recording device 124 so as to display at least part of the data in one embodiment.

The broadcasting usually starts before, simultaneous with or after generation of the radiation and the concomitant exposure of the object or patient.

As a result of the exposure procedure a radiation image of an object is recorded on the now activated photostimulable phosphor screen 124.

Next, the cassette 120 carrying the exposed photostimulatable phosphor screen 124 is fed for read out into a so-called digitizing apparatus 130, where the radiation image is read out. The broadcast meta-data are also read out and are associated with the read out image.

The settings of the read out apparatus are adjusted in correspondence with the read out meta data in one example.

The exposed phosphor screen 124 is subjected to two-dimensional scanning by means of a light beam in the digitizing device 130. Upon scanning, the exposed screen emits image-wise modulated light. This image-wise modulated light is collected and converted into an electric signal representation of the radiation image. The electric signal representation can then be applied to an image processing unit for further processing and/or can be applied to a hard copy recorder or to a display or archive station.

Radiation Detector 126

The radiation detector 126, in one embodiment provided in or on a cassette 120 conveying a radiation image recording device 124 such as a photostimulable phosphor screen. The detector 126 is used to activate the identification device 122 of the associated radiation image recording device, i.e. to provide the selective coupling of the broadcast meta-data to a single radiation image recording device that has or is being exposed The radiation detector 126 is used to detect the presence of radiation and to trigger storage of the broadcast meta-data in storage or identification device 122 associated with a radiation image recording device.

It is usually implemented as one of the following embodiments.

(1) In a first embodiment the secondary emission of radiation emitted by an irradiated object, is used.

This secondary radiation emission emitted by the exposed object is guided to a transducer such as a PIN diode provided with a luminescent phosphor, detected and used to activate a receiver to receive the broadcast data.

A PIN diode is a semiconductor that converts photons into an electric signal (X-ray photons as well as photons that are converted into visible light, e.g. by means of a phosphor).

A color shifting fiber 127 (scintillating fiber, a fiber provided with a phosphor layer) may be provided for collecting the primary high energy radiation and for converting it into light that can be detected by a transducer such as a PIN diode. This can be a two-step process, for example existing of a phosphor that captures X-ray photons and converts them into light within the a first (e.g. blue) wavelength range, this light of the first wavelength (blue) is then converted into light into a second (e.g. green) wavelength range which remains inside the fiber. The green light can be detected at the outer ends of the fiber by a PIN diode that converts the green light into a corresponding electric signal.

(2) In an alternative embodiment the secondary emission by the radiation image recording device 124 (instead of the exposed object) e.g. in the form of light is collected and guided to a transducer such as a PIN diode.

There are different ways to collect the light. Examples are: a fiber positioned around the radiation image recording device which captures light and guides the light towards the transducer, a plan parallel platen assembly, a reflector provided above the image detector.

(3) In an alternative embodiment the high energy radiation itself (x-rays) are used.

The following embodiments are envisaged:
a matrix of transducers (e.g. PIN diodes) positioned at the back of the radiation image recording device 124 (side opposite to side facing the source of radiation) that detect the high energy radiation,
a doped fiber also positioned at the back of the detector to detect the high energy radiation, convert it into light and transport it to a transducer,
a transducer foil (e.g. a foil of solar cells) that detects the high energy radiation at the back of the radiation image recording device.

Broadcast Mechanism

Different energy transfer systems can be used to transfer identification meta-data from the workstation 112, for example, to the identification and storage device 122. Examples are high energy radiation such as electromagnetic radiation, light waves, sound waves such as ultrasound waves etc.

EXAMPLE 1

Infrared (IR) Transmission

The workstation and/or generator console 112 sends, as soon as an X-ray irradiation has taken place, an infrared beam T which is modulated by the identification data, into the exposure room.

The cassette is provided with an infrared transmissive window and a detector of IR rays A. The detected rays are converted into electric pulses that can be interpreted as digital meta-data.

Only the cassette that has also received an X-ray pulse is able to accept these data due to the activation of the radiation detector.

Data are accepted only once because e.g. storing these data reset a flag (trigger) that has been set in response to the detected x-ray pulse.

In case a subsequent exposure is performed on the same cassette, the cassette can store multiple sets and sort them in time. Also the quadrant information will be added to these data.

EXAMPLE 2

Electromagnetic Waves

In this embodiment the workstation (occasionally coupled to the radiology information system) or generator console 112 sends as soon as an X-ray irradiation has taken place, an electromagnetic wave T such as a radiofrequency wave which is modulated by the identification data, into the exposure room.

Every cassette in the exposure room which is provided with an antenna A is able to detect these modulated electromagnetic waves. The detected signals are demodulated and interpreted.

The arrangement is such that only the cassette provided with a radiation detector 126 which has actually detected an X-ray pulse will be activated to accept the data and store the data in a storage device 122.

The data are only once accepted. The arrangements is such that once data are accepted, new data are ignored.

EXAMPLE 3

Ultrasound

In this case the identification data are broadcast into the exposure room by means of modulated ultrasound waves.

Every cassette in the room which is provided with e.g. a microphone will be able to detect the broadcast ultrasound wave. However, the arrangement is such that only the cassette provided with a detector that has also received an X-ray pulse will be able to accept and store the data.

The data are accepted only once. Once the data are accepted, new data are ignored.

Triggering the Exposure

A trigger is used to start the broadcast mechanism.

Figure 2:
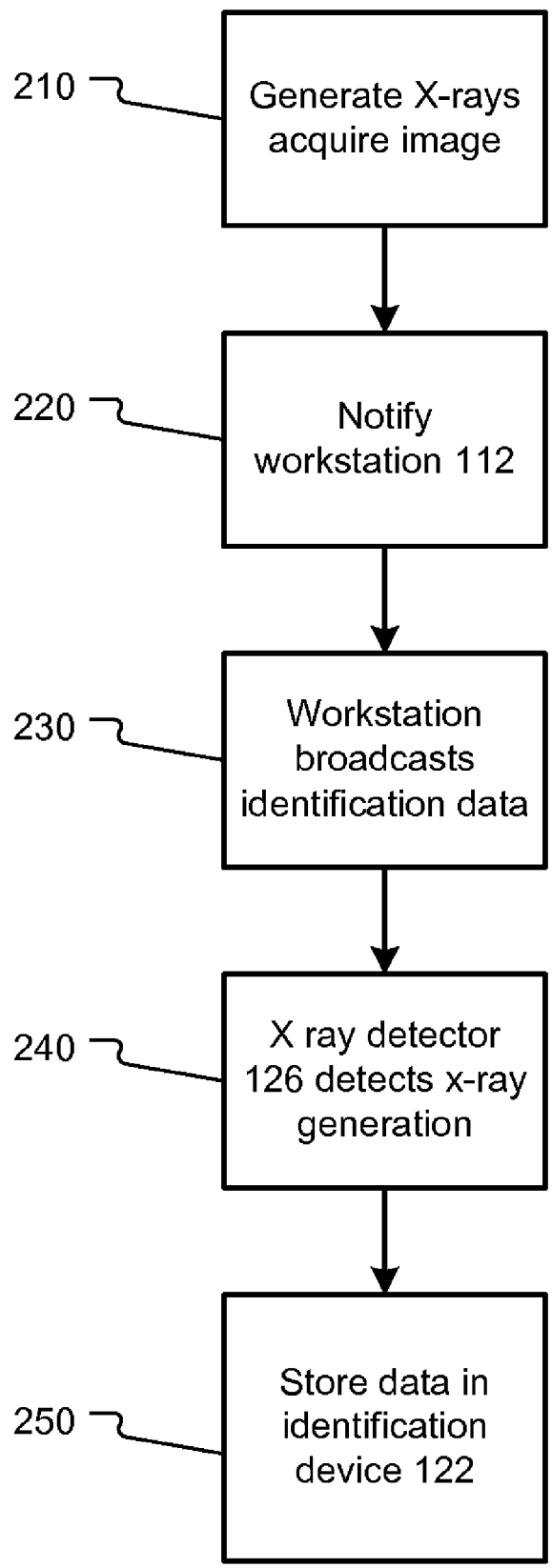
FIG. 2 is a flow diagram of an embodiment of the invention.

With reference to FIG. 2, the following embodiments are applicable to trigger the broadcast mechanism.

A workstation 112 is coupled to the X-ray generator or source 110. As soon as the X-ray generator 110 controls the tube to start an X-ray exposure, in step 210, a signal will be sent to the workstation 112 in step 220 to trigger initiation of the broadcasting of the identification data corresponding with the selected exposure in step 230.

In the vicinity of the x-ray tube, the X-ray detector 126 is positioned which is coupled to the workstation 112. Once this detector detects X-rays emitted by the tube in step 240, it will send a signal to the workstation to trigger broadcasting of the identification data corresponding with the selected exposure, which is stored to the identification device 122 in step 250. Specifically, since only the detector of the cassette that has been exposed detects the x-rays, only that cassette stores the broadcast meta-data data to its identification device 122 since that is the only identification device that has been activated to receive and store the data.

In another embodiment, the identification device 122 functions also as an identification transmitter. Here, the workstation 112 broadcasts a request for an identifier that is associated or with a radiation image recording device 124 or its cassette 120. Upon receipt of the broadcast request, an activated radiation image recording device responds by sending its identifier. Specifically, the radiation detector 126 activates the identification device 122 to transmit the identifier. This sent identifier is associated with the meta-data. The identification device 122 of the radiation image recording device 124 (or cassette 120) that is arranged to respond and will, for example, respond by sending a unique cassette identification number and/or quadrant information (i.e. in which quadrant of the recording device recording has taken place), kVpeak, information regarding the spectrum etc.

While this invention has been particularly shown and described with references to preferred embodiments thereof, it will be understood by those skilled in the art that various changes in form and details may be made therein without departing from the scope of the invention encompassed by the appended claims.

What is claimed is:

1. Method of associating meta-data relating to an x-ray radiation image of an object with the x-ray radiation image, the method comprising:
   providing an x-ray radiation image recording device which is stored in a cassette, and providing a radiation detector in or on the cassette;
   broadcasting the meta-data and activating an x-ray radiation image recording device to record the x-ray radiation image, and
   when the radiation detector detects high energy radiation, the radiation detector triggering a storage device coupled to the x-ray radiation image recording device to store the meta-data.

2. Method according to claim 1 wherein the x-ray radiation image recording device comprises a photostimulatable phosphor screen and wherein the x-ray radiation image is read out of the photostimulatable phosphor screen in a read out and digitizing apparatus.

3. Method according to claim 1 wherein the x-ray radiation image recording device is a direct radiography x-ray image recording device.

4. Method of associating meta-data relating to an x-ray radiation image of an object with the x-ray radiation image, the method comprising:
   broadcasting the meta-data and activating an x-ray radiation image recording device,
   when a radiation detector detects radiation, triggering a storage device coupled to the x-ray radiation image recording device to store the meta-data,
   wherein the radiation detected by the radiation detector is secondary emission of radiation.

5. Method according to claim 4 wherein a scintillating fiber covered with a phosphor layer is provided for guiding the secondary emission to a transducer.

6. Method according to claim 4 wherein said secondary emission is collected and guided by a light guiding fiber.

7. Method according to claim 4 wherein the secondary emission is collected and guided by a light guiding plan parallel platen assembly.

8. Method according to claim 4 wherein the x-ray radiation image recording device comprises a photostimulatable phosphor screen and wherein the x-ray radiation image is read out of the photostimulatable phosphor screen in a read out and digitizing apparatus.

9. Method according to claim 4 wherein the x-ray radiation image recording device is a direct radiography x-ray image recording device.

10. Method of associating meta-data relating to an x-ray radiation image of an object with the x-ray radiation image, comprising:
    broadcasting a request for an identifier of an x-ray radiation image recording device;
    upon receipt of the broadcast request, an activated x-ray radiation image recording device responds by sending said identifier; and
    associating the sent identifier with the meta-data.

11. A method according to claim 10, wherein the x-ray radiation image is recorded by the x-ray radiation image recording device comprising a photostimulatable phosphor screen and wherein the x-ray radiation image is read out of the photostimulatable phosphor screen in a read out and digitizing apparatus.

12. A method according to claim 10, wherein the x-ray radiation image is recorded by a direct radiography x-ray image recording device.

13. An x-ray imaging system comprising:
    a data transmitter for transmitting meta-data regarding a patient and/or an x-ray procedure;
    an x-ray source for generating x-ray radiation for irradiating the patient;
    a cassette including an x-ray image recording device for storing an image of the x-ray radiation from the patient, a radiation detector for detecting the generation of the x-ray radiation, and a data storage device that stores the meta-data when triggered by the radiation detector.

14. A system according to claim 13 wherein the x-ray image recording device comprises a photostimulatable phosphor screen and wherein the radiation image is read out of the photostimulatable phosphor screen in a read out and digitizing apparatus.

15. A system according to claim 13 wherein radiation detected by the radiation detector is a secondary emission of radiation.

16. A system according to claim 13 wherein radiation detected by the radiation detector is a high energy radiation generated by the x-ray source.

17. Method of associating meta-data relating to an x-ray radiation image of an object with the x-ray radiation image, the method comprising:
    transmitting the meta-data in response to activating an x-ray radiation image recording device by generating the radiation to create an x-ray radiation image of the object;
    detecting the generation of the x-ray radiation at a cassette holding the radiation image recording device; and
    activating a storage device coupled to the cassette in response to detecting the radiation.

18. Method according to claim 17, wherein the step of activating the storage device comprises the storage device broadcasting an identifier of the cassette.

19. Method according to claim 17, wherein the step of activating the storage device comprises the storage device storing the meta-data broadcast to the cassette.

20. Method according to claim 17, wherein the x-ray radiation image recording device comprises a photostimulatable phosphor screen and wherein the x-ray radiation image is read out of the photostimulatable phosphor screen in a read out and digitizing apparatus.

21. Method according to claim 17, wherein the x-ray radiation image recording device is a direct radiography x-ray image recording device.

22. Method according to claim 17, wherein the step of detecting the generation of the x-ray radiation includes detecting a secondary emission of radiation.

* * * * *